United States Patent [19]
Tseng et al.

[11] Patent Number: 5,393,854
[45] Date of Patent: Feb. 28, 1995

[54] COLORLESS, PURIFIED POLYMERIZABLE COMPOSITION USEFUL FOR THE PRODUCTION OF CROSSLINKED POLYVINYLPYRROLIDONE

[75] Inventors: Susan Y. Tseng, Staten Island, N.Y.; Philip F. Wolf, Bridgewater, N.J.

[73] Assignee: ISP Investments Inc., Wilmington, Del.

[21] Appl. No.: 234,088

[22] Filed: Apr. 28, 1994

Related U.S. Application Data

[62] Division of Ser. No. 57,378, May 6, 1993.

[51] Int. Cl.6 .......................... C08F 226/10
[52] U.S. Cl. ................................. 526/264
[58] Field of Search ..................... 526/263, 264

[56] References Cited

U.S. PATENT DOCUMENTS 3,933,766  1/1976  Hofmann et al. ............... 526/263

*Primary Examiner*—Joseph L. Schofer
*Assistant Examiner*—Wu C. Cheng
*Attorney, Agent, or Firm*—Walter Katz; Marilyn J. Maue; Joshua J. Ward

[57] ABSTRACT

What is provided herein is a colorless, purified polymerizable composition useful for the production of crosslinked polyvinylpyrrolidone. The polymerizable composition includes about 74–96% by weight vinylpyrrolidone monomer and 4–26% by weight of the isomeric compound 1-vinyl-3(E)-ethylidene pyrrolidone as crosslinker. The polymerizable composition is used to make crosslinked polyvinylpyrrolidone rapidly upon heating the composition at about 80°–120° C. in the absence of base.

2 Claims, No Drawings

COLORLESS, PURIFIED POLYMERIZABLE COMPOSITION USEFUL FOR THE PRODUCTION OF CROSSLINKED POLYVINYLPYRROLIDONE

This is a division of application Ser. No. 08/057,378, filed May 6, 1993.

FIELD OF THE INVENTION

This invention relates to a colorless, purified polymerizable composition useful for making crosslinked polyvinylpyrrolidone, and, more particularly, to an improved process for making crosslinked polyvinylpyrrolidone rapidly in the absence of base.

DESCRIPTION OF THE PRIOR ART

Crosslinked polyvinylpyrrolidone (PVP) is made by popcorn or proliferous polymerization of vinylpyrrolidone (VP), in the absence or presence of crosslinking agents, as described in U.S. Pat. Nos. 3,277,066; 3,306,886; 3,759,880; 3,933,766; and 3,992,562; and by F. Haaf et al. in Polymer J. 17 (1), p. 143–152 (1985), in an article entitled, "Polymers of N-Vinylpyrrolidone: Synthesis, Characterization and Uses". Polymerization of vinylpyrrolidone can occur in the absence of added crosslinker because the requisite crosslinker in the process is formed in situ during the first stage heating of vinylpyrrolidone in aqueous caustic solutions at temperatures $>100°$ C., e.g. at 140° C. These in situ crosslinkers have been identified by gas chromatography and other analytical techniques as 1-vinyl-3-ethylidene pyrrolidone and ethylidene-bis-3-(N-vinylpyrrolidone). These compounds also are believed to be present in very small amounts in reaction mixtures which had been cooled to room temperature. However, after the polymerization was completed, these bifunctional compounds could not be found in the final polymer product. Accordingly, the named bifunctional monomers have been considered to be present only in small amounts during the polymerization and consumed in the process of forming the crosslinked PVP polymer.

Accordingly, an Object of the invention is to provide a colorless, purified polymerizable composition useful for making crosslinked polyvinylpyrrolidone.

Another object herein is to provide a method of making such polymerizable composition.

Still another object is to provide a colorless, purified polymerizable composition consisting essentially of about 74–96% by weight of vinylpyrrolidone monomer and about 4–26% by weight of the isomeric compound 1-vinyl-3(E)-ethylidene pyrrolidone as crosslinking agent.

Among the other objects of the present invention is to provide an improved process for making crosslinked polyvinylpyrrolidone by heating a reaction solution formed by dilution of a colorless, purified polymerizable composition with added vinylpyrrolidone and water.

These and other objects and features of the invention will be made apparent from the following description of the invention.

SUMMARY OF THE INVENTION

What is provided herein is a colorless, purified polymerizable composition consisting essentially of about 74–96% by weight of vinylpyrrolidone monomer and about 4–26% by weight of the isomeric compound 1-vinyl-3(E)-ethylidene pyrrolidone (EVP) as crosslinker. This EVP compound has the formula:

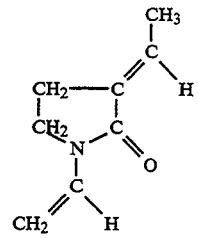

which, in solid form, has a purity of at least 95%, and are white, needle-shaped crystals having a melting point of 59°–61° C.

This isomeric compound exists in the (E) form, which is defined as the isomer in which the methyl group of the ethylidene radical is positioned away from the oxygen atom of the pyrrolidone ring.

The polymerizable composition of the invention is obtained herein from an organic layer formed by reaction of vinylpyrrolidone in a strongly basic aqueous solution. This reaction is carried out in a 2-phase aqueous-organic system, at an elevated temperature, and under vigorous agitation. The reaction product includes an organic layer (top layer) and an aqueous layer (bottom layer). The organic layer then is separated from the aqueous layer and distilled under vacuum. The desired polymerizable composition is obtained as a colorless, purified solution upon distillation of the organic layer.

Crosslinked polyvinylpyrrolidone is produced from the polymerizable composition by the steps which comprise: diluting the polymerizable composition with added vinylpyrrolidone and water to form a predetermined reaction solution, and heating the solution at about 80°–120° C. in an inert atmosphere, under agitation, in the absence of base. The crosslinked polyvinylpyrrolidone polymer product is obtained within about 1–3 hours of such heating, and can be recovered easily without requiring extensive washing to remove caustic and other salts as in the conventional PVP process.

DETAILED DESCRIPTION OF THE INVENTION

In accordance with the present invention, the colorless, purified polymerizable composition consists essentially of about 74–96% by weight of vinylpyrrolidone as monomer and about 4–26% by weight of the isomeric EVP compound as crosslinker. The composition is made by heating a 2-phase reaction mixture comprising an organic phase, which is the vinylpyrrolidone (VP) monomer reactant, and is present in the reaction mixture in an amount of about 25–90%, preferably 40–75%, and, most preferably, about 60% by weight of the reaction mixture, and an aqueous phase which is a strongly basic solution, such as caustic (NaOH or KOH), or a tetraalkyl ammonium hydroxide solution, suitably with a base concentration of about 2–50%, preferably about 5–15% by weight of the mixture.

The reaction mixture then is heated to a reaction temperature of about 120°–170° C., preferably 130°–140° C., in a closed system, under an inert atmosphere, at ordinary or higher initial pressures, suitably at an initial pressure of 0–3 bars of an inert gas, such as nitrogen. The time required to convert VP monomer to the isomeric compound is about 0.5–10 hours, and, usually about 1–3 hours at 140° C. The reaction mixture preferably is subjected to vigorous agitation during the process.

At the conclusion of the reaction, 2 layers are formed as the reaction product. The top layer is a dark brown organic layer which contains about 50–80% by weight of unreacted VP and about 5–30% of the isomeric EVP compound, and small amounts of other organic compounds and traces of water. Typically, this solution contains about 70–75% by weight VP and about 15–20% by weight isomeric EVP. The bottom layer of the reaction product is an aqueous layer which contains small amounts of VP and some EVP.

The organic layer then is separated from the aqueous layer and distilled under vacuum. A colorless, purified polymerizable vinylpyrrolidone composition is obtained upon distillation of the organic layer.

The process of rapid and efficient production of this organic reaction product containing a high concentration of isomeric EVP is based on the following interdependent parameters in the process.

(1) An initial high concentration of caustic catalyst in the reaction mixture, and
(2) Maintenance of the reaction mixture as a two-phase organic/aqueous system throughout the course of the reaction.

Considering both of these parameters, the use of a high (2–50%) caustic concentration has a dual effect. First, the high concentration of a strong inorganic hydroxide causes the aqueous layer to maintain its integrity and "salt out" the organic compounds, most notably, vinylpyrrolidone. Such is not the case in conventional PVP syntheses using a low concentration of caustic solution in which the aqueous and organic phases merge. Secondly, the high caustic concentration in the process of the invention accelerates the reaction of VP to EVP. Indeed, the caustic, which is a catalyst for the formation of EVP from VP, is consumed through reaction with 2-pyrrolidone, a by-product of the reaction. The 2-pyrrolidone, in turn, is readily hydrolyzed by base to sodium 4-aminobutyrate (4-AB), which is not a catalyst for EVP formation. However, (4-AB), being water soluble, can serve as the salt necessary to maintain the 2-phase system in the process.

Transfer of the vinyl moiety of the VP monomer which is necessary for EVP synthesis appears to take place in the invention process at or near the organic-water interface of the 2-phase reaction system. Once the VP transfer is complete, the slightly acidic 2-pyrrolidone by-product can drift into the basic aqueous phase while EVP can move into the organic medium. In fact, both the strong base and other salts are present overwhelmingly in the aqueous layer during the process. The conversion of 2-pyrrolidone to 4-AB in the presence of aqueous base reduces the concentration of base in the organic phase, thereby avoiding an undesired further reaction of EVP to ethylidene-bis-vinylpyrrolidone (EVBP) and other related organic molecules.

The colorless, purified polymerizable composition of the invention then is obtained by fractional distillation of the organic reaction product. Suitably, distillation is carried out by heating the organic layer to below 40° C. under 1–2 mm Hg vacuum to remove traces of water and low boiling organic compounds from the product. Then the pot temperature is increased to about 54°–65° C. while maintaining the vacuum condition. Thereafter, the residue is flash distilled at this temperature at 1–2 mm Hg. The distillate is collected and analyzed. The distillate is colorless and consists of VP and isomeric (E) EVP in a purity of >99%. The VP content of the composition is about 74–96% by weight and the isomeric EVP content is about 4–26% by weight.

This colorless, purified polymerizable composition then is diluted with added vinylpyrrolidone monomer and water to form a reaction solution having a predetermined concentration of monomer, crosslinker and water preferred for the rapid production of crosslinked polyvinylpyrrolidone. Preferably the reaction solution is diluted to a concentration of about 25–85% by weight of vinylpyrrolidone, about 1.5–5% EVP and about 15–75% water.

The reaction solution then is heated at about 80°–120° C., preferably about 100° C., for about 1–5 hours, preferably about 2 hours, in an inert atmosphere upon agitation to form crosslinked polyvinylpyrrolidone in high yield.

The invention will now be illustrated with reference to the following examples.

EXAMPLE 1

A 1-l reaction vessel equipped with a reflux condenser and a mechanical stirrer was charged with 100 g of vinylpyrrolidone (VP) monomer and 300 g of B.F. Goodrich Caustic 20 solution (20% NaOH). The 2-phase reaction mixture was given a blanket of nitrogen and heated to 100° C. where it was held for 5 hours while stirring vigorously at 800 rpm. The reaction product consisted of a top organic layer and a bottom aqueous layer. The two layers were separated. 80 g of a brown organic layer was collected; it contained 15% by weight of isomeric (E) EVP and 75% by weight of vinylpyrrolidone, and small amounts of other organic compounds and water.

EXAMPLES 2–3

The procedure of Example 1 was followed using a stainless steel Buchi reactor as the reaction vessel with an initial nitrogen pressure in the reactor of 3 bars at room temperature. The reaction was carried out at 140° C. for 2 hours using a charge of 240 g of VP, 80 g of 50% NaOH solution and 80 g of distilled water (Ex. 2), and 320 g of VP and 80 g of 50% NaOH solution (Ex. 3). A brown organic product was obtained in both examples.

EXAMPLE 4

80 g, 200 g and 260 g of the organic layer as obtained in Examples 1–3, respectively, were purified by fractional distillation. First the organic product was heated to below 40° C. under 1–2 mm Hg vacuum. Traces of water and low boiling compounds thereby were removed from the organic product. Then the residue was flash distilled and the purified composition was collected at 54°–65° C. under 1–2 mm Hg. A total of 50, 120 and 150 g of a colorless purified composition was collected. This composition was comprised of about 92% by weight of VP and about 8% by weight of the isomeric (E) EVP compound.

EXAMPLE 5

62.7 g of the colorless, purified polymerizable composition of Example 4 was diluted with 57.3 g vinylpyrrolidone and 20 g of water to form a reaction solution of 80% vinylpyrrolidone, 2.5% EVP and 17.5% water.

The reaction solution was charged into a Buchi reactor at 0.3 bar nitrogen pressure (<18 ppm $O_2$), under 800 rpm agitation, and heated for 2 hours at 100° C. The product was crosslinked polyvinylpyrrolidone in an amount of 108 g (90 % yield).

While the invention has been described with particular reference to certain embodiments thereof, it will be understood that changes and modifications may be made which are within the skill of the art. Accordingly, it is intended to be bound only by the following claims, in which:

What is claimed is:

1. A colorless, purified polymerizable composition consisting essentially of about 74–96% by weight of vinylpyrrolidone and about 4–26% by weight of 1-vinyl-3 (E)-ethylidene pyrrolidone.

2. A composition according to claim 1 consisting essentially of about 85–95% by weight of vinylpyrrolidone and about 5–15% by weight of 1-vinyl-3(E)-ethylidene pyrrolidone.

* * * * *